United States Patent
Nur et al.

(10) Patent No.: US 9,491,206 B2
(45) Date of Patent: Nov. 8, 2016

(54) SIMPLE VIDEO COMMUNICATION PLATFORM

(71) Applicant: Aetonix Systems, Ottawa (CA)

(72) Inventors: Ruqia Mohamud Nur, Nepean (CA); Richard Kelly Wiles, Plano, TX (US); Georgiy Shibaev, Kanata (CA); Michel Paquet, Ottawa (CA)

(73) Assignee: Aetonix Systems, Ottawa (CA)

( * ) Notice: Subject to any disclaimer, the term of this patent is extended or adjusted under 35 U.S.C. 154(b) by 0 days.

(21) Appl. No.: 14/670,512

(22) Filed: Mar. 27, 2015

(65) Prior Publication Data
US 2015/0281294 A1    Oct. 1, 2015

Related U.S. Application Data

(60) Provisional application No. 62/051,036, filed on Sep. 16, 2014, provisional application No. 62/037,731, filed on Aug. 15, 2014, provisional application No. 61/971,929, filed on Mar. 28, 2014.

(51) Int. Cl.
| | |
|---|---|
| *H04N 7/15* | (2006.01) |
| *H04L 29/06* | (2006.01) |
| *H04N 7/14* | (2006.01) |
| *H04N 5/232* | (2006.01) |
| *A61B 5/00* | (2006.01) |
| *G06F 3/0488* | (2013.01) |
| *G06F 19/00* | (2011.01) |

(52) U.S. Cl.
CPC .......... *H04L 65/403* (2013.01); *A61B 5/0022* (2013.01); *A61B 5/747* (2013.01); *G06F 3/04886* (2013.01); *G06F 19/3418* (2013.01); *H04N 5/23206* (2013.01); *H04N 7/141* (2013.01); *H04N 7/147* (2013.01)

(58) Field of Classification Search
USPC ...................................................... 348/14.03
See application file for complete search history.

(56) References Cited

U.S. PATENT DOCUMENTS

| | | | |
|---|---|---|---|
| 6,020,915 A * | 2/2000 | Bruno | H04M 3/42221 348/14.09 |
| 2007/0186002 A1 | 8/2007 | Campbell | |
| 2008/0068447 A1 | 3/2008 | Mattila | |
| 2008/0129816 A1 | 6/2008 | Mattila | |
| 2010/0110160 A1 | 5/2010 | Brandt | |
| 2012/0054691 A1* | 3/2012 | Nurmi | G06Q 10/10 715/854 |
| 2013/0215214 A1* | 8/2013 | Dhopte | H04N 7/157 348/14.08 |

(Continued)

OTHER PUBLICATIONS

International Search Report, PCT/IB2015/052290, 4 pages, date of mailing Jul. 27, 2015.

(Continued)

*Primary Examiner* — Creighton Smith
(74) *Attorney, Agent, or Firm* — Nixon Peabody LLP

(57) ABSTRACT

A system offering simplified bi-directional video communication between a user and a device of a pre-configured one or more persons of interest includes a touch display with a pictorial representation of each of the one or more persons of interest. The touch display is configured to establish the bi-directional video communication with a selected one of said persons of interest in response to a single touch of the pictorial representation of the selected one of the persons of interest. In one implementation, the system includes a monitoring device positioned to monitor one or more biometric parameters of the user, and saving the biometric data on a server for processing.

8 Claims, 12 Drawing Sheets

(56) References Cited

U.S. PATENT DOCUMENTS

2014/0269625 A1* 9/2014 Surface ............ H04W 36/0083
370/332
2015/0173670 A1* 6/2015 Simon .................. A61B 5/4806
702/150

OTHER PUBLICATIONS

International Written Opinion, PCT/IB2015/052290, 5 pages, date of mailing Jul. 27, 2015.

* cited by examiner

SIMPLE VIDEO COMMUNICATION PLATFORM

CROSS REFERENCE TO RELATED APPLICATION

This application claims the benefit of U.S. Provisional Application No. 62/051,036, filed Sep. 16, 2014, U.S. Provisional Application No. 62/037,731, filed Aug. 15, 2014 and U.S. Provisional Application No. 61/971,929, filed Mar. 28, 2014, each of which is hereby incorporated by reference herein in its entirety.

FIELD OF THE INVENTION

The present disclosure relates to video communication, and in particular to a simple station enabling video communication and telemetry information gathering.

BACKGROUND

Seniors and people with special needs often face problems related to depression and health issues due to stress and social isolation. Many of these peoples live alone in a special care residence or at home. Often the fact that they are remote from family members leads to health issues. Overtime people lose interest to social activities, are getting socially disconnected, and get into a mode of expectation of family members showing up to visit them. This situation of social isolation leads to depression. There is a need to improve their communication with one or more POI (e.g. family member, friend, health care provider, residence staff).

Many families have a member at home that required continuous professional health care support. Often the professionals are remote and need to visit family required time. There is a need for a virtual remote care support to reduce health care cost while providing a more responsive service to patient in remote home. There is a need for a simple video communication system that works seamlessly across different devices and operating systems.

BRIEF SUMMARY

In accordance with one embodiment, a system offering simplified bi-directional video communication between a user and a device of a pre-configured one or more persons of interest includes a touch display with a pictorial representation of each of the one or more persons of interest. The touch display is configured to establish the bi-directional video communication with a selected one of said persons of interest in response to a single touch of the pictorial representation of the selected one of the persons of interest. In one implementation, the system includes a monitoring device positioned to monitor one or more biometric parameters of the user, and saving the biometric data on a server for processing.

In accordance with another embodiment, a point-to-point video communication system between two devices includes a signaling component based on Message Queue Telemetry Transport (MQTT) protocol, and a video communication component based on Real-Time Communication (RTC), wherein the signaling component is used to establish an RTC communication between the devices. One implementation includes a telemetry component to gather telemetry information based on the MQTT protocol.

The foregoing and additional aspects and embodiments of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the disclosure will become apparent upon reading the following detailed description and upon reference to the drawings.

Figure 1:
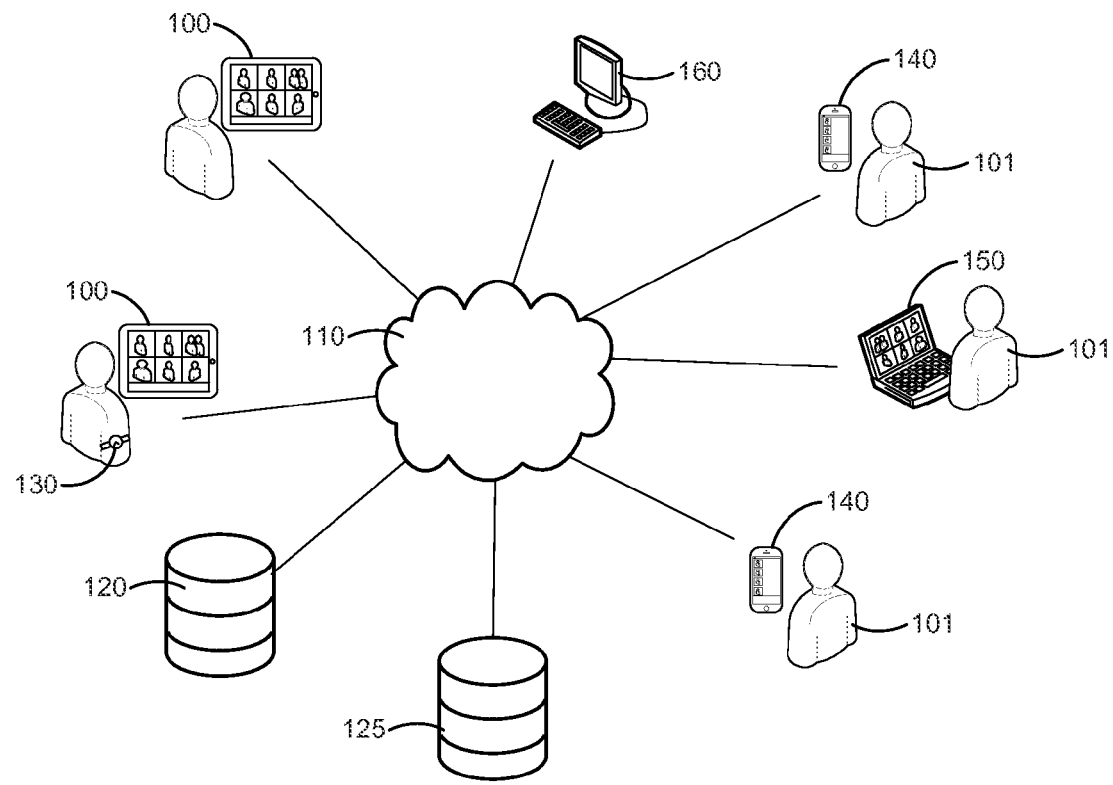
FIG. 1 is a high level diagram of the components of the system.

While the present disclosure is susceptible to various modifications and alternative forms, specific embodiments or implementations have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of an invention as defined by the appended claims.

DETAILED DESCRIPTION

A first embodiment, a Simple Video Station (SVS) is provided to seniors and people with special needs (referred to herein generically as "users"). The SVS has minimal uner interaction capabilities other than allowing to establish video/voice communication with predetermined POI (POI). Transparently, the SVS can optionally perform several other functions such as monitoring health information provided by biomedical telemetry systems or detecting emergency situation like fall or inactivity detection. The SVS also provide the user with medication reminders, emergency call, and other basic function.

The SVS is designed for users with limited mobility, minimal technical knowledge and possibly limited by cognitive impairment.

FIG. 1 gives an overview of the solution connectivity. One or more SVS 100 users can communicate with one or more predetermined POI 101. A software communication platform for biomedical telemetry and any other telemetry, which is managed by an integrated cloud computing solution for data analytics.

The SVS 100 allows a user to establish for video/audio connection with a single tap on a picture, corresponding to a POI 101. The POI 101 receives the call using an application on a smartphone or tablet 140 or on a computer 150. The SVS also has optional radio support for Zigbee®, Bluetooth®, and WIFI® allowing connection to Internet over the air and to telemetry devices using Bluetooth® and Zigbee®. The SVS and applications are configured via a configuration database 125. The SVS connects to telemetry 130 devices surrounding the user which allow continuous transfer of data related to the user and/or the environment where the user lives via a telemetry database 120 to different applications. A central or distributed server 160 may also be used for configuration and monitoring of one or more SVS that are deployed. The configuration 125 and telemetry database 120 may be on the same file system. They may also be part of the server 160.

The data is transferred to a database 120 via a network 110, and is stored for analysis such as trending, data mining, and analytics. Notification, alarm, or recommendation can be provided to the POI based on the analysis. With that information, a POI can decide if an action is required or if everything is normal. Similar information is also available to family members which allow the families to be aware and assured of condition of relative. Assuming an abnormal situation, the system can notify a POI for immediate action and prevent undesired situation. If a doctor needs to be consulted, the SVS allow video/audio connection to a POI enabling the user to have a discussion on the situation without having to move outside of their apartment. The SVS allows three-way conferences with any POI, for example, a health professional, a family member, and a user.

The SVS can optionally have sensors (e.g. Near Field Communication token reader) to record when visits are done by a POI to the user. This information is maintained in a database. The profile of the POI may optionally be loaded on the SVS when they are visiting allowing them access to their contacts. Optionally, any POI can load their profile on the SVS in order to access their contacts and make call. The profile loading could be made by, for example, a pre-determine gesture on the POI's picture of the SVS. The SVS can optionally be used in kiosk mode, whereby the SVS is loaded with a profile (POI or USER) when an identification token is detected by a sensor. The profile is removed when the person walks away from the SVS.

The SVS incorporates touch screen technology, displays a set of fixed and predefined pictures on which a simple touch enables a video/audio connection to the desired POI The intent is to connect families in a very easy way and to address some of the social isolation issue for users. The SVS also enables virtual care and helps to limit health care professional visits saving time and money while offering more responsive service. The SVS is also a reference point for time, date, season, and reminder on health recommendation like time for drugs, and time for special treatment. The SVS is also transparently to the user a bridge for the telemetry and sensors technology. The data gathered from the SVS, is analyzed and acted on when needed to secure the environment. The SVS also comes with profile setting to enable more flexibility in configuration. In this case, a list of pictures can be used, with swiping to navigate, and on screen keyboard search. With a more flexible profile, the SVS allows instant message and emotions to be sent between a user and the POI.

The SVS generally comprises:
Touch Screen
Speakers
Microphone
WebCam
Ethernet connection
Radio: Bluetooth®, Zigbee®, WIFI®
Stand to support the SVS or wall mounted
Optional output port to connect to larger screen TV
Optional audio jack to connect to earphones.

The SVS is remote configuration by an admin including the selection a profile between full flexibility (for more experienced users) or simple experience (for the user).

Figure 3:
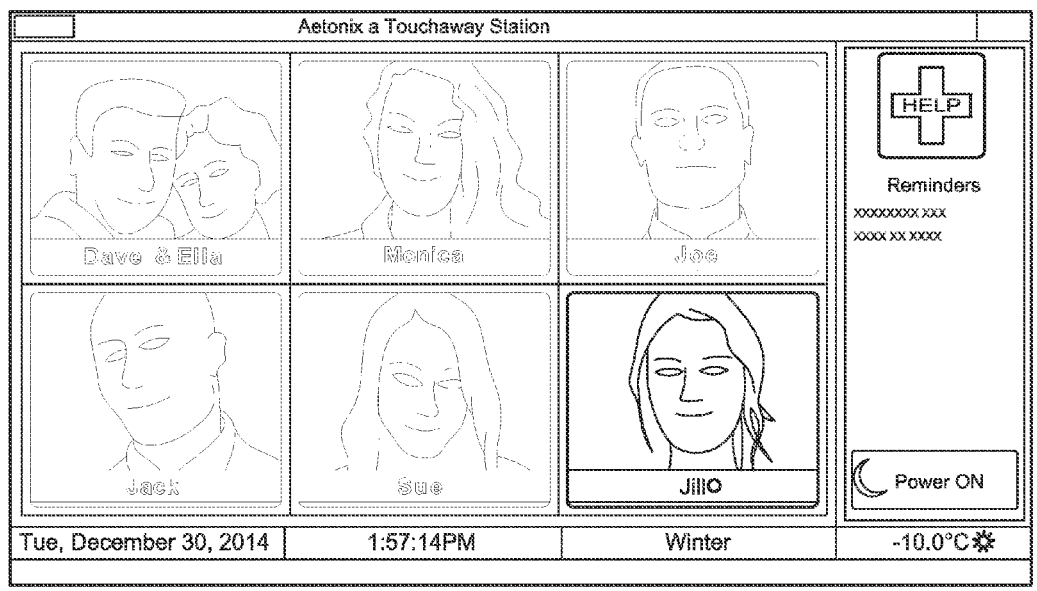
FIG. 3 is an example of an SVS screen.

In Simple experience profile, the limited functions available comprise:

i. Selection of the POI to be displayed as people to be called
ii. User login for the SVS (this map to the person using the SVS)
iii. Pairing of the telemetry devices or sensors
iv. Adjustment of date, time, and season
v. Desire selection of display for availability
vi. Time for emotion text to be displayed
vii. Auto detection of faces with camera movement
viii. Auto detection of voice alert
ix. Auto detection of emergency call on SVS
x. Configuration of emergency call (911 or health care staff)
xi. Auto answer video/audio on call
xii. Auto video/audio on emergency call
xiii. Auto alert to specific user on emergency call
xiv. Auto alert on certain biomedical/vital signs
xv. Enable recording of video/voice message
xvi. Language setup
xvii. Configuration of temperature units In full flexibility profile (All the above and the following):
xviii. All POI listed for a user are displayed and swapping is used to navigate
xix. Enable keyboard access for Instant messaging & Emotions
xx. Voice recording for message
xxi. Continuous picture gallery display
xxii. Internet browsing
xxiii. Music players
xxiv. Games support
xxv. Instant video clip playing In simple profile, the SVS displays the pictures of the POI configured and allow selection for call. If a POI is not available, the photo is grayed out or disabled as shown in FIG. 3. If available, the photo is in relief and looks like a button that can be pressed. The photo also has the name of the person on it.

The SVS also allows for a POI to send emotion message to be displayed on SVS. A POI can optionally send a text or instant message that gets displayed on the picture for a configurable time. In the simple experience profile, the SVS doesn't allow for a reply to make it simple on users. In the full flexible profile, the Instant message & emotion can be sent from the SVS.

The SVS allows for call scheduling. The POI using the application can optionally schedule a video call with a user. At the scheduled time, an alarm is emitted on the SVS to notify the user that a call is about to happen.

The SVS also has voice recognition to allow connection through voice command. A user can initiate a connection by talking and mentioning the POI to be called or to place an emergency call.

The SVS always ensures a voice-only connection if bandwidth for video is not sufficient. The SVS has a Webcam that allow video capture and transmission. The webcam preferably recognize facial movement and adjusts based on the position of the user.

Emergency call (911 or staff call) is placed if screen is consistently touched for a predetermined time. On an emergency call and if configured, the video turns on automatically. On an emergency, a list of desired POI can be notified of the situation. An alert can be sent to each of them.

The SVS has recognizes if a user has touched several time in few seconds a picture. This can be considered as a single touch. This allows for users with agility problem to use the systems (Parkinson is an example) effectively.

The SVS, on connection, displays the person been called in a quality size. Another touch on the end call button or the picture ends the call.

The SVS may be integrated with a fall/inactivity detection bracelet and calls an emergency automatically on fall detection or inactivity detection or simply when an emergency button press on the bracelet. The SVS generates warning and then alarm on the inactivity situation.

The SVS calls an emergency number automatically on vital signs alarm. Example, on a pulse change going lower than expected, the SVS calls an emergency number based on configuration.

The SVS also provides one or more reminders to the user. The reminder can be programmed remotely by a POI. Reminders can be scheduled in the future and optionally recurring. Reminders can be social activities, drugs and appointment.

The SVS can also support marketing message to provide the user with information on the product of its interest.

The SVS provides the user with reminder on the telemetry maintenance if required (e.g. low battery).

The SVS can receive video call and rings like a phone until it is answer or the caller hang-up. Display show the person calling in larger form with "Call received." The SVS answers. The SVS has the capability to record a video/audio message if enable and if phone not answer. The SVS has the capability to record a video/audio communication on a one touch on a record button while in a call. An animation may be played on the screen to remind the user how to activate the function.

If enabled at configuration time, the SVS displays in bigger form (bigger picture) when the user is near the screen with his finger but has not selected (touch).

The SVS allow incoming call from a POI even if it is not listed as a picture on the SVS, as long as it is in a the list of the users. If not in the list, the SVS can optionally reject the call.

To avoid getting into complicated states, the SVS has a special approach to get into configuration mode. Touching bottom left corner of the screen for 7 times quickly bring the SVS in configuration mode. Any other combinations or times can also be used. The power down button can also optionally be disabled as well, the sleep mode can also optionally be disabled avoiding cases where the SVS is turned off or in a state that is difficult for the user to manage. As another embodiment, special gestures applied to the logo on the screen can enable different configuration modes.

The SVS supports remote debug/diagnostic, if enabled in the configuration. The SVS can have a software update remotely. Update can be scheduled at a preferred time using the configuration menu and is transparent to the user.

Optionally, the SVS keeps track of statistics. The SVS monitors which POI is called more often than other. This can be used to change the picture of the POI used on the SVS dynamically. Access to the log file can be done through the configuration menu. The SVS tracks the time spent on connection between a user and a POI to have history and trends.

The SVS, if enabled, allows display of the current telemetry on screen in place of some POI pictures.

The server 160 monitors one or more SVS to ensure they are always connected and in the proper login state. If connection is lost, the server notifies a POI or a system manager. If the SVS loses the login state, it retries automatically for a predetermined number of times before it sends a notification.

Remote control, configuration and updating of the SVS may use encrypted channels to avoid loss of personal information.

The SVS can optionally automatically answer a call to allow a POI to evaluate the situation by video with a user that is not answering a call.

The user optionally wears a wearable device referred herein as a wrist remote control (WRC) to enable remote control capability of the SVS. A call can be received and answered from the WRC enabling the video SVS to accept the call. The WRC can optionally be used to receive reminder (the same reminder that are available on the SVS). The WRC optionally allows a POI to detect falls based on its sensitive positioning device. The WRC provides an emergency call link to the SVS for immediate video capability and emergency call. The WRC optionally allows selection of a contact to call and initiate a call on the video SVS. The WRC optionally allows reception of a personal message from a POI (e.g. text message). The same message can be displayed on the video SVS. The WRC allow fall detection generating an alarm through the SVS to the POI. The WRC may also enable inactivity detection leading to warning and then alarm.

Figure 2:
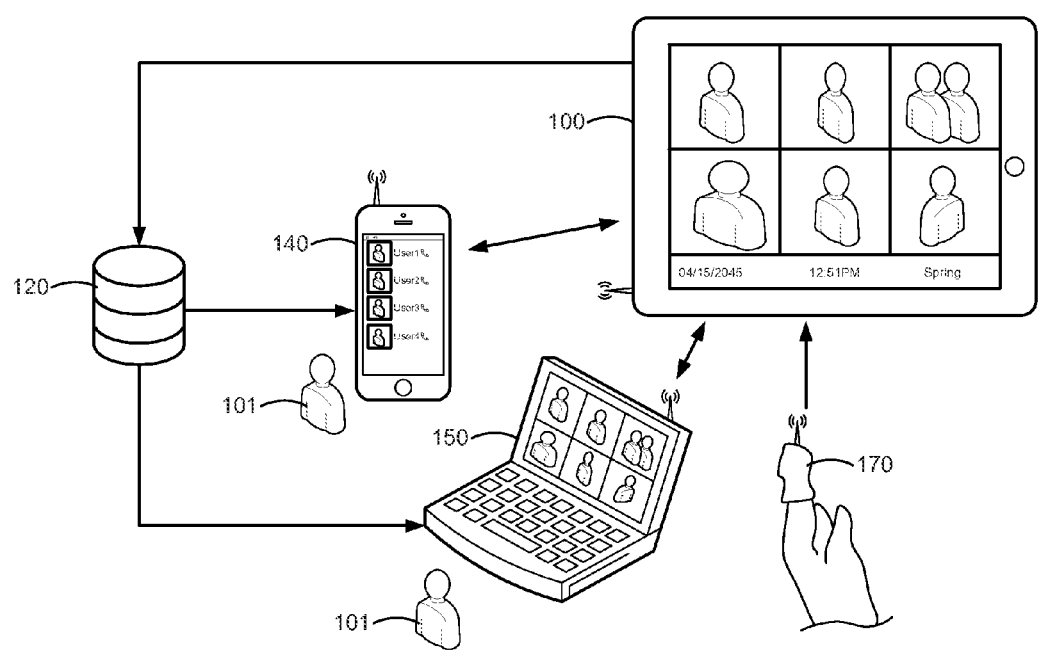
FIG. 2 is an example of the application structure

A WRC can optionally be used by the POI to, for example, receive emergency call and the biomedical data of a user, receive biomedical trend data for a user or receive reminder/tasks to be completed The user of the SVS can communicate with another SVS or any other mobile phone or computer via an application used by a POI available through any application stores. An application is also available for download on a PC or Mac. FIG. 2 provides an example of applications running on computers 150 and smartphone 140 for POI 101. The user may wear a telemetry sensor 170 which communicates transparently with the SVS 100 to transmit the telemetry information which is stored in a database 120 and retrieved by the POI application 150, 140.

The SVS can be configured into a kiosk mode with a badge reader allowing a user to tag in have its profile loaded. When this is done, the SVS can be used by different users, for example in a library.

The SVS can optionally be setup into multi-users where a user selects their profile and login.

Application

The application is used to communicate between a SVS user and a POI. The application configuration management, through a web portal or on the device, comprises:
   1. Selection of language
   2. Creation/Configuration of the POI
   3. Configuration of the POI and user list
   4. Upload of picture for the POI
   5. Login & password management
   6. Creation of one or more group for one or more user for availability status for each group.

The application presents the POI with a user login screen. After the login action, the POI is presented with a list of users and other persons of interest with the associate pictures (see FIG. 2). The pictures are gray out or normal indicating availability or any other color combination showing availability. Gray out mean that the user or POI are NOT available. Beside each user or POI is a connect button, a texting message button, or telemetry button. If telemetry access is enabled, the POI can select the telemetry and see the history and current user data. With the telemetry enabled, the POI can be notified of alert if configured in the SVS.

The application allows the user or POI to define availability per user, per group, or for all. This is useful in the case that a user keeps calling back due to memory challenges like Alzheimer. The POI logoff or set is availability status to unavailable if this is necessary. In another embodiment, a timer may be configured for each POI and the user is prevented from calling back a POI if they just completed a conversation earlier than the expiry of the timer.

In order for the SVS, or application, to connect between users and POI, a communication server is required. The communication server can be the same server as the configuration server or a different one. It can be centralized or distributed. A server with all user and POI is provisioned and refreshed regularly or each time a new user or POI is added. The concept of "user in the cloud" is used. Anyone using the application or the SVS has a user identifier and password and a picture. The profile of the user or POI is stored in a configuration database 125.

If a connection needs to be established, the server signals the connection and sets up a peer to peer direct connection between the user and POI.

Optionally, the data related to telemetry is stored only for a maximum of days of history. Optionally the telemetry database is located on private network and secured with encryption.

In order to establish connection between two SVSs or with an application, the system needs to go through a signaling process. After signaling completed, the peer to peer video connection is established. Prior to that, a server in the cloud (the configuration server) does the mapping from one user to the POI. The user initiating a call has a communication identification (commID). This commID is pushed to the server. The users or POI that are logged in all have a unique commID. The signaling handles the connection between the originator of the call and the recipient of that call. When signaling is completed, a connection gets established, and then a peer to peer connection takes place with video and audio. The server can be a public (e.g. Google®) server or a private one. The protocol WEBRTC is an example of an open source software platform that can be used. Any other protocol that interoperates between any platforms can be used.

Telemetry/Sensors Platform

The SVS is designed to enable connectivity with telemetry equipment and sensors that can communicate through Zigbee® or Bluetooth®. Any wearable Biomedical devices or any in room telemetry or sensors equipment that comply to the API of an open platform, can be connected to the SVS and have the data transferred to the user database and be stored/analyzed by qualify staff. The remote configuration of the video SVS, allows administrator to add protocol compliant telemetry or sensors equipment.

The SVS has alarm detection, which flags issues with telemetry data as configured to one or more POI. With the telemetry data transferred to the network, POI can review to identify anomalies. The system can also be configured to notify POI of unexpected behaviors. As example, an irregular pulse can trigger an alarm. Another example is an element open on a cook top for long time can trigger an alarm if some telemetry is in place for monitoring such event.

The telemetry data is transferred on a continuous basis while the user is collocated with the telemetry sensor and the SVS. When outside of reach, the telemetry sensor may buffer the data in memory until the next available time of connectivity with the SVS.

The SVS, with the telemetry information, may report to POI the mood of a person. Using heart rate, temperature trends, and potentially body humidity level, the system indicate to the POI how the user is doing and if the person is suitable for a call in the case where the person may be limited by cognitive impairment. The feature helps with ensuring that a call is made to a user when in its best condition. The POI is optionally notified by a red, yellow, or green status light on the application.

The SVS is pushing continuously data to a server and database for storage and analytics. The server can analyze trends per user for each telemetry items and based on notification configuration, notified POI if undesired situation happen. The server can also do some data mining, some pattern analysis, and provide with potential warning of human changes or environment change. The data trending, mining observation, and notification are store in the database and can be accessed by POI to analyze and provide recommendation to a user.

Since the data is per user, it is possible to configure that one or more POI, access at the data. Family can maintain a close status on users. The data is useful for health staff like doctors to see trends and behaviors to diagnose a situation.

The servers and database can be implemented as a standalone system for a residence or cloud services where the servers and databases are offered remotely as a service to the residence. A residence may decide to have a server infrastructure local and have the data private while the communication is still possible.

Since it is also important for residence management to monitor staff interaction with resident (user) and to ensure that face to face service is offer, telemetry/sensor are used to monitor visits to each apartment. The badge reader or identification card, can connect to the SVS and push information on visit time and staff identification. This way information per staff and per user is available to management to improve its service if required. It is also extremely useful for audit as the data is available and reports can be issue with the administrative application.

An administrative application is available to selected POI.

From the administrative application, several functions are available:

a) Administrator: This professional can add or delete user or people of interest. It can enable debugging, or network performance monitoring. It can configure databases and servers. He can set privilege for other user. It has access to all system data. The admin can also configure a SVS and force a reset of configuration of a SVS.

b) Health specialist: This professional has access to all user data and can use trending, data mining, history, and current data. This professional can set new threshold or alarms for a given user. This professional can set the reminders and the schedule of the reminders. This professional can request from administrator a reset of the data.

c) Management: This professional has access to statistics, and report on user interaction but does not have access to the private data except if allowed by a user and the health specialist. This professional has access to all staff data and interaction with resident. He can set notification alarms for staff scheduled visits with resident and ensure that they are done. This professional can print report for audit purposes d) Staff support: This professional provides assistance to the user to setup the telemetry. They have access to server to ensure that telemetry data is active. This professional also received telemetry alarms like battery low, malfunction, and can take action to repair telemetry. This professional also gets alarms on environment telemetry like water leakage or cook top open. In this case, the professional can take immediate action. This professional can add user or person on interest remotely. A SVS can be programmed remotely with the expected configuration and list of POI. Typically this professional helps in setting up the SVS after the sales of the service.

The administration application allows to input manual data by hand to the database for each user. For example, data from a visit can be stored per user based. This data can be used by health specialist and can be report on.

Figure 4:
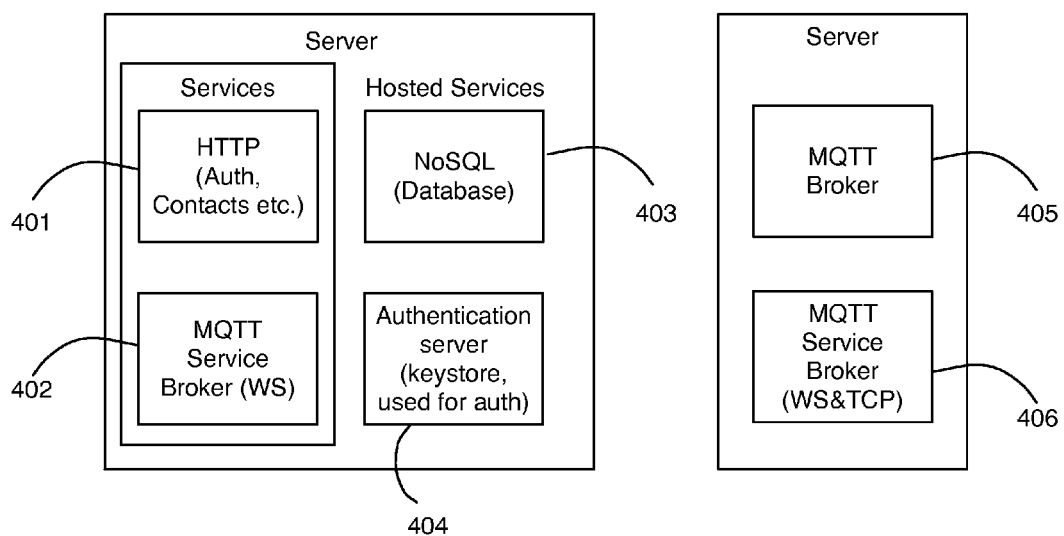
FIG. 4 depicts an example of the modules used to deploy simple point-to-point video where multiple applications are distributed on one or more servers.

FIG. 4 depicts an example of the modules used to deploy simple point-to-point video where multiple applications are distributed on one or more servers. The embodiment includes a document oriented database and a key value store (type NOSQL) 403, an authentication server to control access 404, a Message Queue Telemetry Transport (MQTT) broker server 405 used for messaging between processes for websockets and TCP/IP sockets.

The HyperText Transfer Protocol (HTTP) module 401 enables HTTP request to get contact list, device setting, and information on contact invitation for the SVS. All device type could emit an HTTP request to get information from the server The MTTQ service broker 402 provides SVS with an Application Programing Interface (API) that enables desktop applications or IOS applications and SVS station to send/receive MQTT messages to/from other devices in the network. The API is a custom broker built with an open source library. The broker 402 also performs authorization and request for authentication.

The MQTT Android service broker 406 provides SVS with an API that enables Android app to send/receive MQTT messages to/from other devices in the network. The API is a custom broker built with an open source library. The broker also performs authorization and request for authentication.

The database 403 enables the SVS platform with a document and graph type database (NoSQL). The database maintains all administration information about the users, status, preferences for the system, preference of type of call, contact list, pictures, voice mail, video messages, logs on users about health.

The authentication server 404 provides a server mechanism to authenticate any access to data. It is used for MQTT message and HTTP request. Any failure to comply causes an error of authentication and data is not accessible.

The MTTQ broker 405 is an open source library. This container of software enables messages to be created, delivered, and diagnosed. The WebSocket and TCP brokers are communicating with the MQTT broker for messages.

Figure 5:
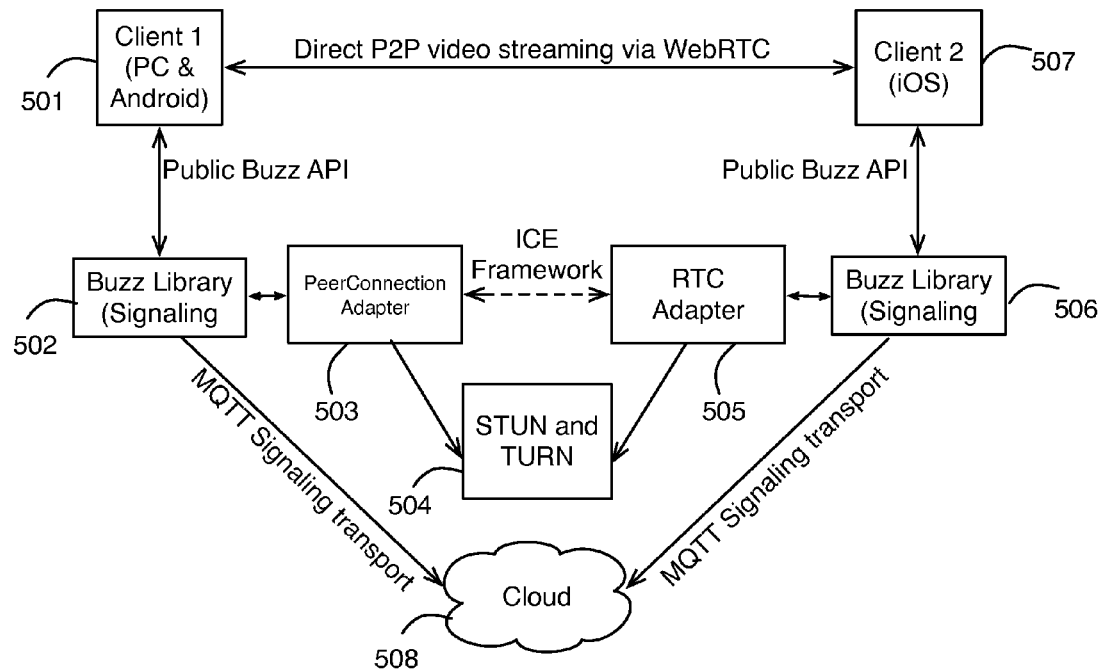
FIG. 5 provides an overview of the call flow between 2 clients.

FIG. 5 provides an overview of the call flow between 2 clients. The buzz library enables signaling between the clients using the MQTT transport layer. Messages are exchanged until protocol agreement. RTC is then used over the Internet Communication Engine (ICE) framework to establish the peer to peer (P2P) connection path. When done, the client communicates over P2P. Session Traversal Utilities for Network address translation (STUN) and Traversal Using Relays for Network address translation (TURN) servers are used into the P2P connection to overcome firewalls and routing issues.

A device 501 of a user establishes a peer to peer video audio call. The SVS application running on the device presents an interface to the user to make its call and interact with the signaling engine library through the SVS public API. On user request, like pressing on a call button, the SVS device application executes the proper algorithm and call APIs of the signaling library to start the process of a call.

The SVS application running on an user device, include the signaling library 502 which enables the application to signal the far end device through MQTT messages to setup a connection. The signaling library 502 algorithm takes care of identifying the room ID for the communication, gets authorization to communicate from the servers, prepares the adequate MQTT message with the ID of the callee, and sends the required messages. The signaling also takes care of the reception of a request for a call. The signaling library 502 acknowledges a request. Finally, the library 502 also exchange on the Session Description Protocol (SDP) and the ICE candidate to be used for the communication between the 2 users. Any message been sent from the library is sent on the cloud (Internet) with the proper destination address. After the signaling phase is completed and that the room could be joined by both user's device, the signaling library proceed with establishing a peer to peer direct connection by using the "Peer Connection Adapter" represented in FIG. 5.3

The PeerConnection Adapter 503 provides the SVS system with an abstraction layer of the WEBRTC primitives. The simple API enables the signaling library to establish, or close calls very easily. When a communication is established between 2 devices, the ICE candidate establishes the direct P2P streaming via WEBRTC. It also enables error handling and fault detection. The adapter is not available for IOS devices.

The STUN and TURN component 504 of the SVS systems handles discovery of IP address behind firewalls and routers. The STUN is a standardized set of methods and a network protocol to allow and end host to discover its public IP address if it is located behind a network address translator. TURN is a protocol that assists in traversal of NAT or firewalls for multimedia application. Adding this component 504 into the SVS system ensures that an IP is known and reachable.

The SVS system may comprise an RTC Adapter for iphone Operating System (IOS®) 505. This adapter provides equivalent function of the PeerConnection adapter 503 for Android and PC. This abstraction layer provides access to the WEBRTC primitive on IOS. The RTC phone adapter also provides an API that enables the signaling library to establish, or close calls. When a communication is established between 2 devices, the ICE candidate is set and used to establish the direct P2P streaming via WEBRTC. It also enables error handling and fault detection. The adapter is only available for IOS devices.

An IOS signaling library 506 is used for IOS connections.

Devices communicate over the internet 508 for their private P2P video/audio call.

Figure 6:
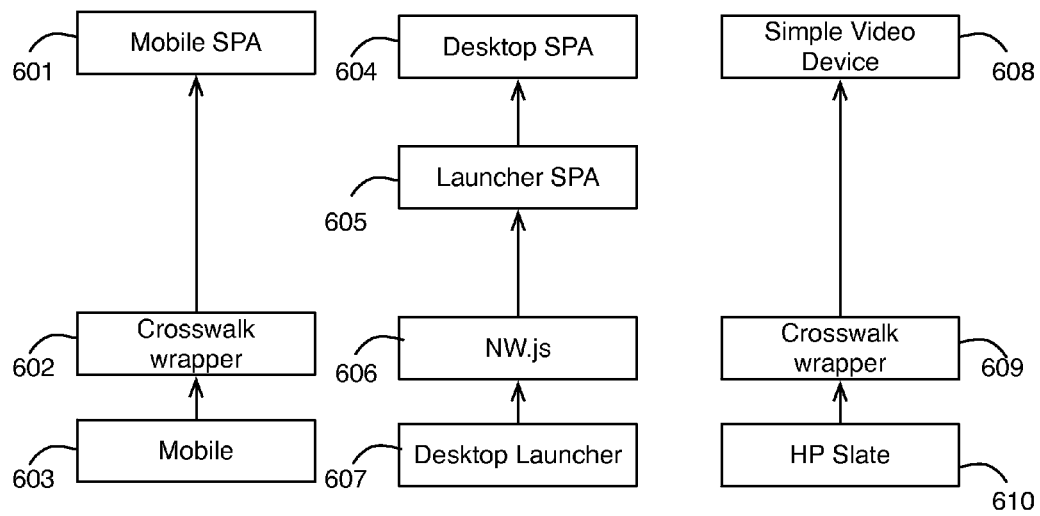
FIG. 6 is an example of a Single Page Application (SPA) approach used for the smartphone, hub and simple video device.

Referring to FIG. 6, a Single Page Application (SPA) approach is used for the smartphone, hub and simple video device. For mobile Android or the simple video device, a Crosswalk wrapper is used. For IOS devices, another RTC platform is used, and for the desktop, a Node webkit is used along with a launcher page.

A Single WEB Page Application (SPA) 601 for the mobile device is used to create mobile content using, for example, the Crosswalk wrapper for the Android devices. Support for HTML5, CCS3, Javascript is available.

The crosswalk wrapper 602 is a simple implementation of a Crosswalk library for the SVS systems for the android devices. It enables the application to run, for example, HTML5, Javascropt, and CCS3.

The SPA is executed on a mobile device 603.

For desktop, a Single WEB Page Application (SPA) for Desktop device (MAC and PC) 604 is provided. The web content is created using the NodeJS webkit. Support for HTML5, CCS3, Javascript is available.

The launcher of Single Web Page Application 605 checks if new content/new version is available from the content server and refresh with the latest at start time of the application.

A public source code such as NW.js 606 enables to develop fast, scalable network application like SVS. This platform builds on Chrome's javascript runtime. Any other platform with similar functionality can be used.

A desktop launcher 607 launches the execution of the SPA on the PC or MAC.

For the SVS 608, a Simple WEB Page Application (SPA) is created using the Crosswalk wrapper 609 for the Simple Video device. Support for HTML5, CCS3, Javascript is available. The SPA is executed on a video device 610 with optionally reduced capabilities.

Figure 7:
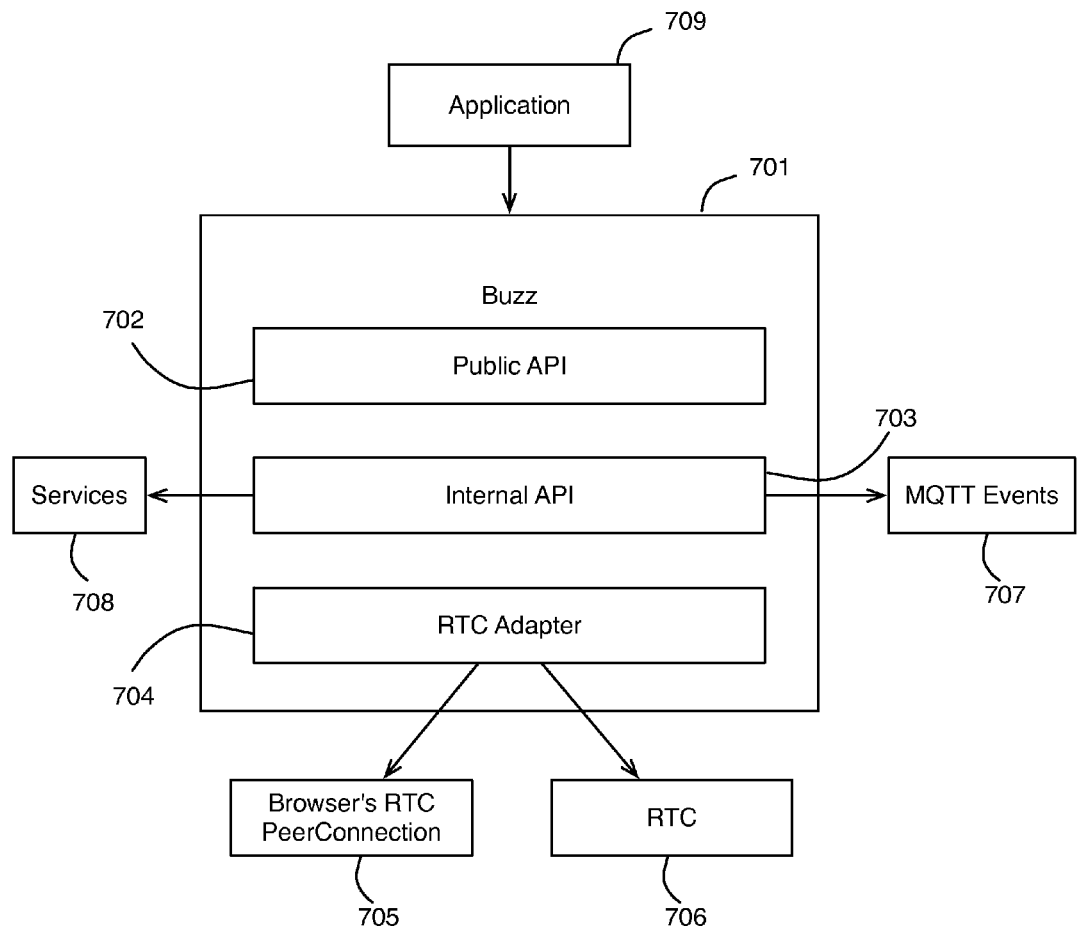
FIG. 7 shows how a signaling library is used to establish peer to peer connection between users.

In FIG. 7, a signaling library 701 used to establish peer to peer connection between users. Its public API enables the application 709 to manage calls between remote device and itself. The library has an internal API 703, a public API 702 and has an RTC adapter 704 facilitating the use of RTC 706 for P2P 705. The library uses MQTT events 707 for discovery of actions to be taken and uses services 708 to send messages, get authorization and authentication, and to send HTTP requests.

The signaling Library container 701. The library has a public API used by the applications, an internal set of API, and provides an RTC adapter to connect to RTC PeerConnection for IOS and PC or to RTC adapter for IOS.

The Public API 702 is used by the application to establish a call with a user on a different device. The Internal API 703 is used by the signaling library. This is only used internally.

The RTC adapter 704 of the signaling library creates an abstraction to the specific RTC layer for each device.

The signaling library 701 registers to listen to events that happen with the delivery MQTT messages 707. When a message is delivered, MQTT events are raised to enable the signaling library to take action.

The signaling library is taking advantage of several services 708 offered. The service for authentication or authorization is provided to the signaling library. Service of registration and database access is also available. Any other services may be offered to the signaling library.

Figure 8:
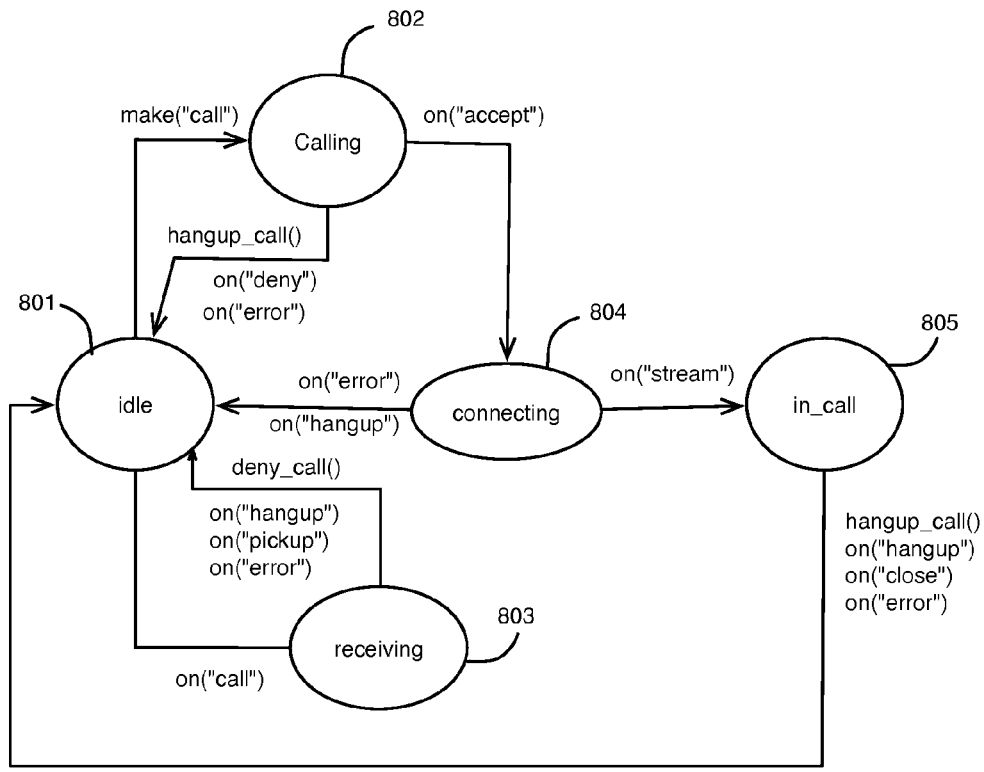
FIG. 8 shows an example of the state machine for establishing a peer to peer call between devices for the SVS system.

FIG. 8 shows an example of the state machine for establishing a peer to peer call between devices for the SVS system. Five states are enabling the SVS system devices to take the proper actions. Many of the state transition are due to MQTT message exchange between two devices based on the action of the user.

The initial state 801 of the application on a device is the "Idle" state. In this state, no call has been initiated and calls could be received or made.

The "calling" state 802 of the application represents that a user on a specific device using the SPA has trigger a call by pressing the call function. The API make_call( ) will transition from "Idle" state to "Calling" state and the proper MQTT message to be sent to the far end. If the user select the hang-up call function or an error happens or the far end user denies the call, the state machine for this device returns to "Idle" state. If the far end user accepts the call, the process of signaling starts and the SVS device transitions to "Connecting" state.

The "receiving" state 803 of the application represents a user receiving a call on its device from a remote user. The application moves to this state based on a MQTT message received. If the application is in idle state and a "call" message arrived, the state machine moves to "receiving" state. While in "receiving" state, if the user accept the call, the application for the moves to "connecting" state. In the case that the call is deny by the user the state moves to "Idle." If the far end user stop calling (hangup) than the state moves to "Idle." If the user receiving the call, answer the call from a different device, the current device SVS state moves to "Idle." Finally error message on connecting moves back to"Idle".

The "connecting" state 804 for the represent the period in time where the connection is getting establish. The signaling is getting done and the WEBRTC peer to peer is getting setup. Assuming a successful connection, and the video stream is available, the SVS system moves to "in_call" state. If an error happen while connecting or if one of the user hangup, the state moves back to "Idle"

The "in_call" state 805 is the desired state for ensuring that a call is in progress and the application is connected in VIDEO/AUDIO with another user. If any of the user hangup, or if connection failed, the SVS state moves back to "Idle"

Figure 9:
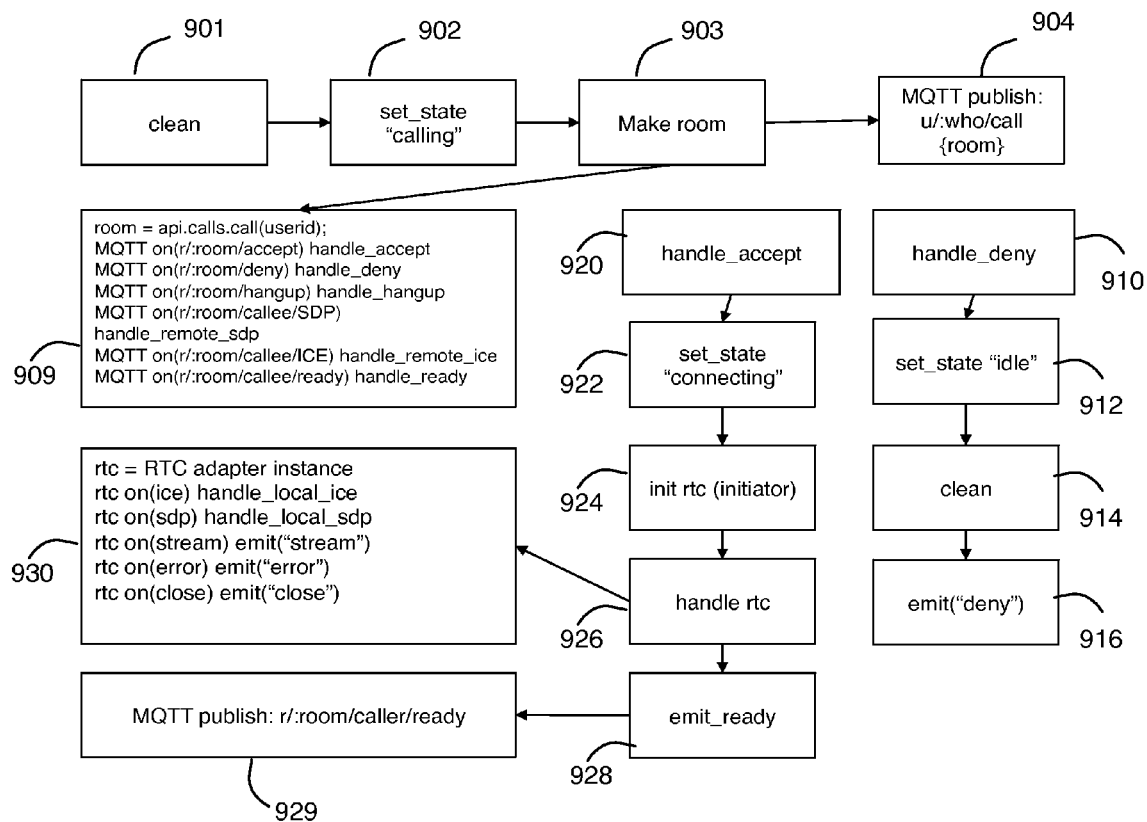
FIG. 9 shows an example of a call is being made between 2 devices.

FIG. 9 shows an example of a call is being made between 2 devices. The first step is done is to clean the current state 901 of the state machine to make sure that the previous call's data has been freed from memory. When this is completed, the state is set to "calling" 902.

After the cleaning activity has been completed, the process will proceed on creating a new communication "Room" 903 by calling a server API. Then it starts listening on MQTT events related to the room and to the callee. The MQTT messages are as followed 905:
  room=api.calls.call(userid);
  MQTT on(r/:room/accept) handle_accept
  MQTT on(r/:room/deny) handle_deny
  MQTT on(r/:room/hangup) handle_hangup
  MQTT on(r/:room/callee/SDP) handle_remote_sdp
  MQTT on(r/:room/callee/ICE) handle_remote_ice
  MQTT on(r/:room/callee/ready) handle_ready The SVS system sends an MQTT message to the callee 903 with the room information and who the call is from. The form of the message is MQTT publish: u:/who/call (room).

The SVS system handles calls to be denied 910. If a callee denies the call, the state is set to Idle 912 for the caller, the state is cleaned 914, and the rest of the applications receive a deny event 916.

The SVS system accepts the call 920 by setting the state is set to "connecting" 922 and the RTC connections is setup 924. The room get notified that the caller is ready for sending RTC information 926 by "emit function" 928: MQTT publish: r/:room/caller/ready 929.

A new RTC adapter is created 930 and set to be initiator of the call. Listeners are added for various events from the adapter. The RTC messages are:

rtc=RTC adapter instance
rtc on(ice) handle_local_ice
rtc on(sdp) handle_local_sdp
rtc on(stream) emit("stream")
rtc on(error) emit("error")
rtc on(close) emit("close")

Figure 10:
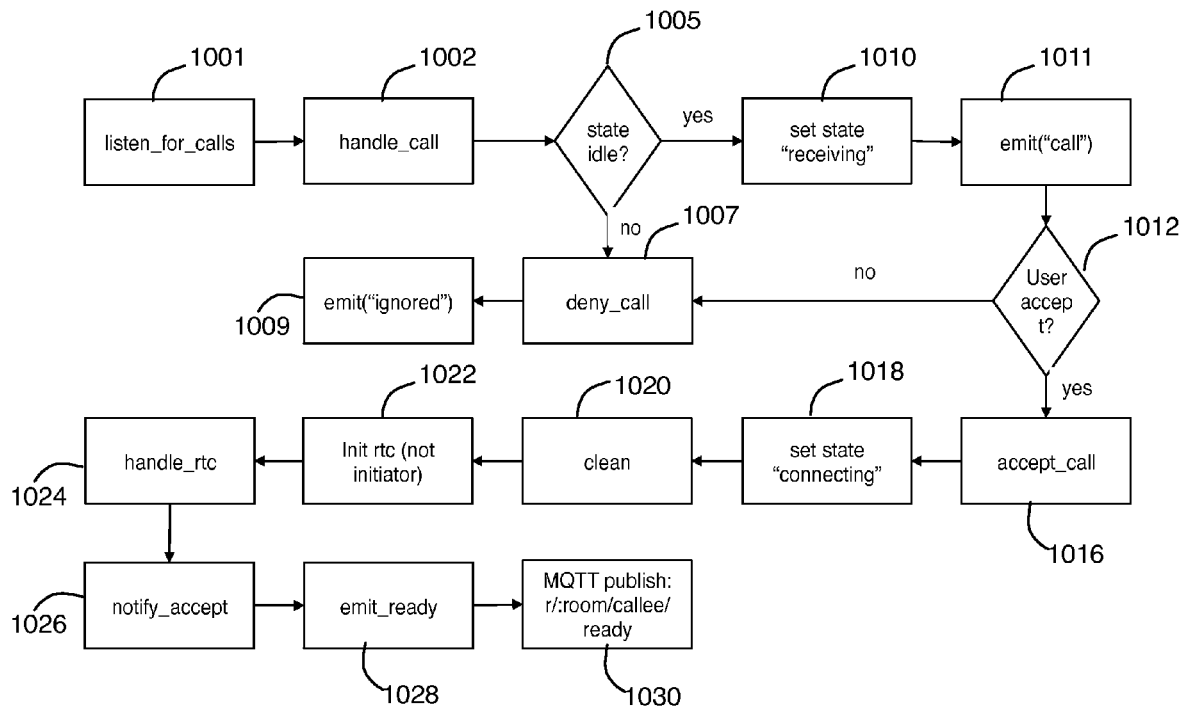
FIG. 10 shows an example process for a device to receive a call from another user.

FIG. 10 demonstrates the process for a device to receive a call from another user.

When the application on a device of the SVS system first boot, it subscribes the MQTT topic for incoming calls 1001. Once data is published to that topic, it is processed as a new incoming call 1003.

The application on the device is listening for calls 1001. Whenever a new call arrives 1002, the application checks to see if it is currently in the idle state 1005. If the state of the device is not in the "Idle" state 1007 when a call is received, then the call gets denied and the caller gets a message over MQTT informing that the call is rejected 1009.

If the state of the device is in "Idle" state when a call is received, the state get set to "receiving" 1010 and the user get prompted 1012 to accept 1016 or deny the call 1007 through the proper presentation layer of the user interface. If the user denies the call using the SVS system 1007, than the same process as above is performed.

If the user accepted the call 1016, then the state is set to "connecting" 1018, the state is cleaned 1020, the RTC adapter is created 1022, events for the adapter are listened on 1024, the caller is notified that the call has been accepted 1026, and the callee emits an event to the room 1028 saying that they are ready to exchange the RTC communication data 1030.

Figure 11:
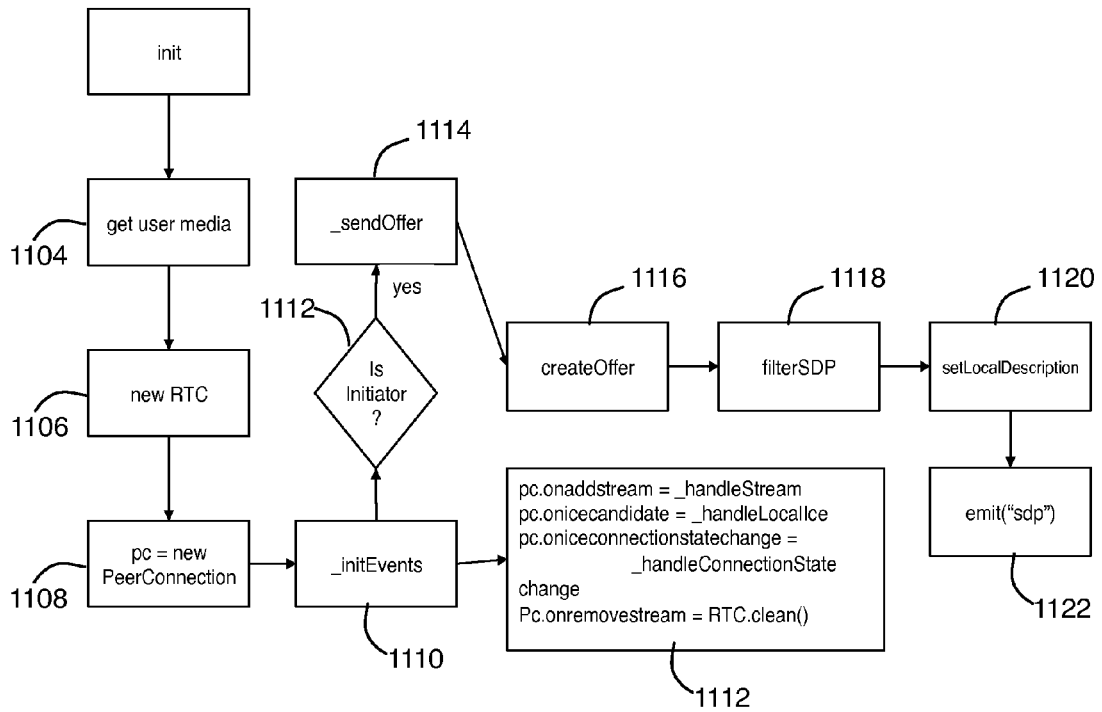
FIG. 11 describes the process of setting up RTC adapter in desktop browser.

FIG. 11 describes the process of setting up RTC adapter in desktop browser.

The desktop application gets the camera/microphone media stream 1104, creates a new RTC instance 1106, and attaches a new PeerConnection instance of RTC adapter 1108.

The SVS systems can add listeners 1110 to the PeerConnection to handle receiving new media stream, ICE candidate, and SDP data. It also handles closing and cleaning the RTC adapter 1112.

If RTC adapter has been setup as the initiator of the call 1112, the adapter creates the initial SDP string and sent it to the client 1114. The SDP string of the initiator's machine is created 1116. The SDP string describes the video/audio formats that are supported (bitrate, resolution, compression etc). The SDP settings are modified 1118 to give more fine-grained customization of the SDP parameters for further optimization. The local SDP string is set 1120. The SDP string is emitted and sent via MQTT to the callee 1122.

Figure 12:
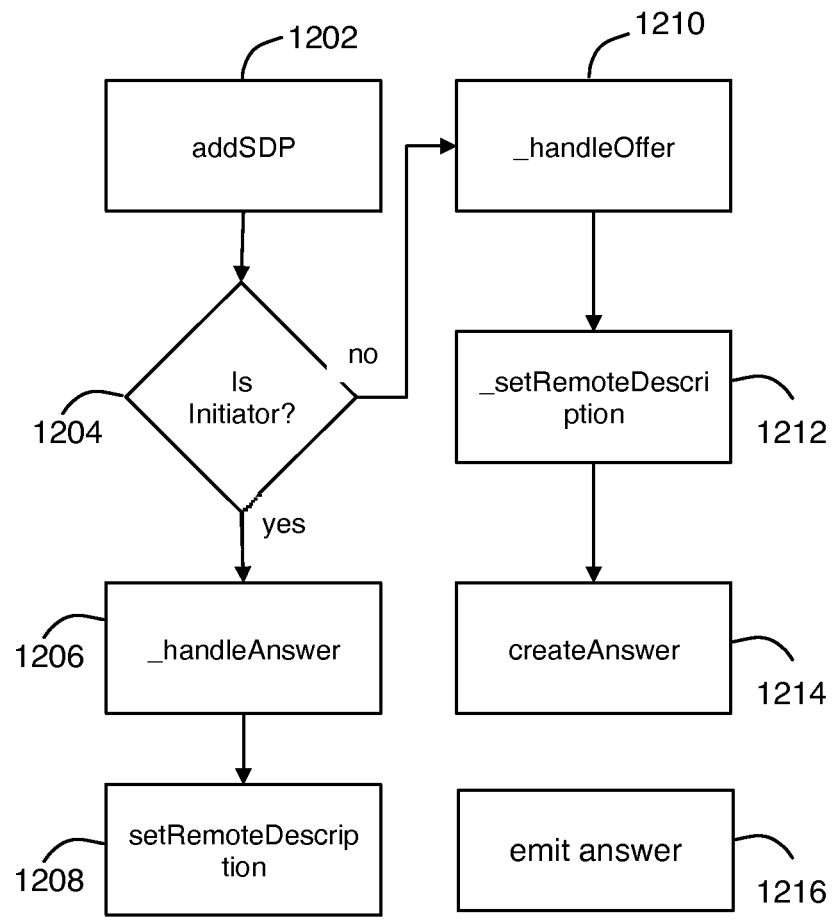
FIG. 12 describes the process from the application running on a desktop and receiving call information from another device.

FIG. 12 describes the process from the application running on a desktop and receiving call information from another device. SDP information is received 1202 from the other device and it is received over MQTT. If the RTC adapter is the initiator 1204, then it processes the SDP as the "answer" 1206 and set the remote description of the PeerConnection 1208.

If the RTC adapter was not set up as the initiator 1204, then it processes the SDP as the "offer" 1210, set the remote description 1212, then generates its SDP answer 1214 and emit the answer to the application to be sent over MQTT 1216.

Although the algorithms described above including those with reference to the foregoing flow charts have been described separately, it should be understood that any two or more of the algorithms disclosed herein can be combined in any combination. Any of the methods, algorithms, implementations, or procedures described herein can include machine-readable instructions for execution by: (a) a processor, (b) a controller, and/or (c) any other suitable processing device. Any algorithm, software, or method disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire algorithm and/or parts thereof could alternatively be executed by a device other than a controller and/or embodied in firmware or dedicated hardware in a well known manner (e.g., it may be implemented by an application specific integrated circuit (ASIC), a programmable logic device (PLD), a field programmable logic device (FPLD), discrete logic, etc.). Also, some or all of the machine-readable instructions represented in any flowchart depicted herein can be implemented manually as opposed to automatically by a controller, processor, or similar computing device or machine. Further, although specific algorithms are described with reference to flowcharts depicted herein, persons of ordinary skill in the art will readily appreciate that many other methods of implementing the example machine readable instructions may alternatively be used. For example, the order of execution of the blocks may be changed, and/or some of the blocks described may be changed, eliminated, or combined.

It should be noted that the algorithms illustrated and discussed herein as having various modules which perform particular functions and interact with one another. It should be understood that these modules are merely segregated based on their function for the sake of description and represent computer hardware and/or executable software code which is stored on a computer-readable medium for execution on appropriate computing hardware. The various functions of the different modules and units can be combined or segregated as hardware and/or software stored on a non-transitory computer-readable medium as above as modules in any manner, and can be used separately or in combination.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

What is claimed is:

1. A system offering one-touch bi-directional video communication between a user of a device and a pre-configured one or more persons of interest, said system comprising:
   a touch display with a fixed pictorial representation of each of the one or more persons of interest;
   a monitoring device positioned to monitor one or more biometric parameters of the user, said monitoring device in communication with said touch display, wherein said touch display transmits said biometric parameters to a database for processing by one or more of said persons of interest;
   wherein said touch display is configured to establish said bi-directional video communication with a selected one of said persons of interest in response to a single touch of the fixed pictorial representation of said selected one of said persons of interest.

2. The system of claim 1 further comprising:
a signaling component based on Message Queue Telemetry Transport (MQTT) protocol, and
a video communication component based on Real-Time Communication (RTC).

3. The system of claim 1 further comprising:
wireless connectivity between said touch display and said monitoring device.

4. The system of claim 3 wherein said wireless connectivity is established using one or more of Bluetooth, Zigbee and WIFI.

5. The system of claim 1 wherein said fixed pictorial representations is programmed by a system administrator.

6. A method for establishing simplified bi-directional video communication between a user and of a device of and a pre-configured one or more persons of interest, said method comprising:
displaying, via a touch display, a fixed pictorial representation of each of the one or more persons of interest;
monitoring, via a monitoring device, one or more biometric parameters of the user;
transmitting, via the monitoring device, said biometric parameters to the touch display;
transmitting, via the touch display said biometric parameters to a database for processing by one or more of said persons of interest;
establishing said bi-directional video communication with a selected one of said persons of interest in response to a single touch of the fixed pictorial representation of said selected one of said persons of interest.

7. The method of claim 6 further comprising:
configuring, by a system administrator, said fixed pictorial representations.

8. The method of claim 1 further comprising:
signaling a request to establish the bi-directional video communication using a Message Queue Telemetry Transport (MQTT) protocol, and
in response to said signalling, enabling the bi-directional video communication using a Real-Time Communication (RTC) protocol.

* * * * *